United States Patent

Kulkashi et al.

[11] Patent Number: 5,098,388
[45] Date of Patent: Mar. 24, 1992

[54] VERESS NEEDLE ASSEMBLY

[76] Inventors: Richard Kulkashi, 9 Jonathan Dr., Tinton Falls, N.J. 07753; Matthew P. Szapucki, 65 Kingsley Rd., Kendall Park, N.J. 08824; Stephen A. Grochmal, 10 Elmwood Dr., Milltown, N.J. 08850

[21] Appl. No.: 694,670

[22] Filed: May 2, 1991

[51] Int. Cl.[5] ............................................. A61M 5/00
[52] U.S. Cl. ................................. 604/158; 604/164
[58] Field of Search ............... 604/117, 157, 158, 170, 604/165, 164

[56] References Cited

U.S. PATENT DOCUMENTS

| | | | |
|---|---|---|---|
| 1,527,291 | 2/1925 | Zorraquin | 604/158 |
| 2,623,521 | 12/1952 | Shaw | 604/170 |
| 3,727,613 | 4/1973 | Sorenson et al. | 604/165 |
| 4,379,458 | 4/1983 | Bauer et al. | 604/264 |
| 4,601,710 | 7/1986 | Moll | 604/165 |
| 4,627,841 | 12/1986 | Dorr | 604/158 |
| 4,654,030 | 3/1987 | Moll et al. | 604/165 |
| 4,808,168 | 2/1989 | Warring | 604/158 |
| 4,850,973 | 7/1989 | Jordan et al. | 604/157 |
| 4,869,717 | 9/1989 | Adair | 604/51 |
| 4,902,280 | 2/1990 | Lander | 604/165 |
| 4,931,042 | 6/1990 | Holmes et al. | 604/164 |
| 4,973,312 | 11/1990 | Andrew | 604/165 |

Primary Examiner—Paul J. Hirsch
Attorney, Agent, or Firm—Watov & Kipnes

[57] ABSTRACT

A Veress needle instrument consists of a housing serving as a handle, a hollow needle having one end mounted in the housing and a pointed other end, a tube slidably mounted within the needle, the tube having one end sealed off and a side wall hole proximate the sealed end, the other end of the tube passing through the hollow needle and into the length of a passageway of a spring biased bobbin mounted in the housing, with the other end being secured in the passageway. The passageway of the bobbin opens into a porthole thereof for receiving a fluid coupling through a hole in the top end of the housing, thereby permitting fluid to be passed directly between the tube and the fluid coupling. The bobbin is normally biased toward the bottom end of the housing, for causing the one end of the tube to extend away from a pointed end of the needle with the side hole of the tube unobstructed. When a force directed against the end of the tube causes it to retract into the needle, the bobbin moves toward the top end of the housing, causing a colored portion of the bobbin to protrude out of the hole in the top end of the housing, for providing a visual indication that the one end of the tube has retracted into the needle.

22 Claims, 6 Drawing Sheets

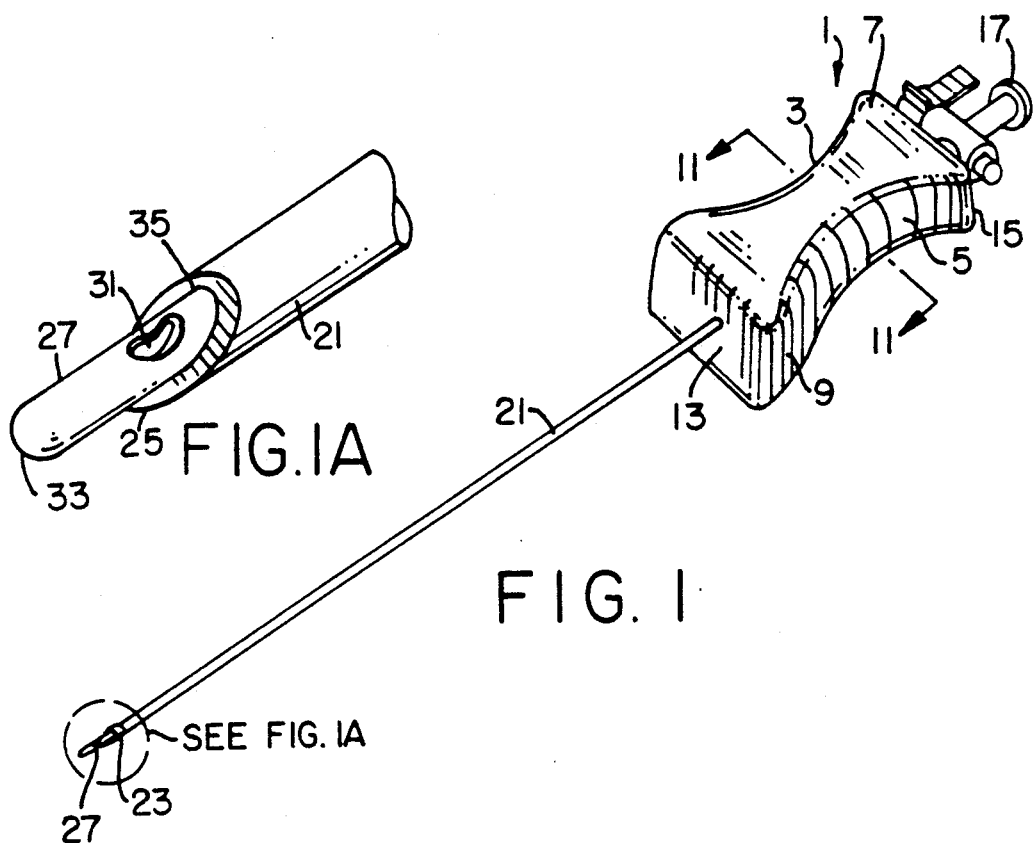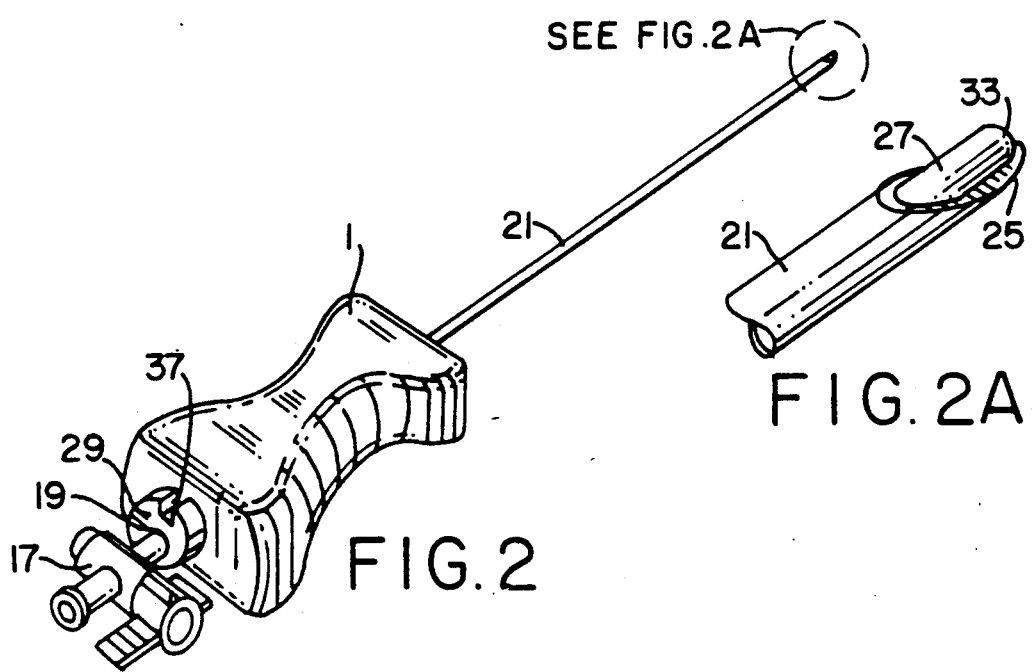

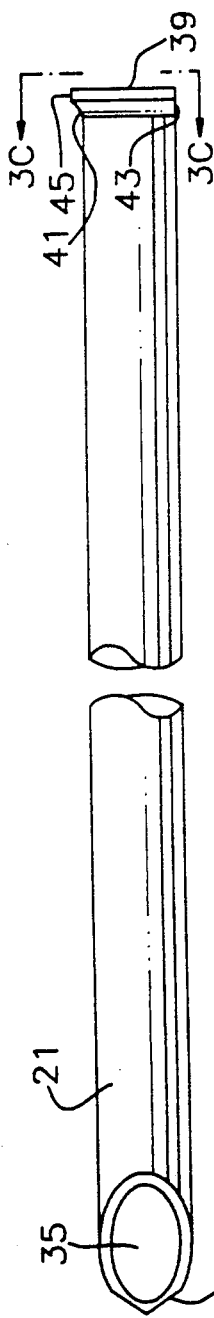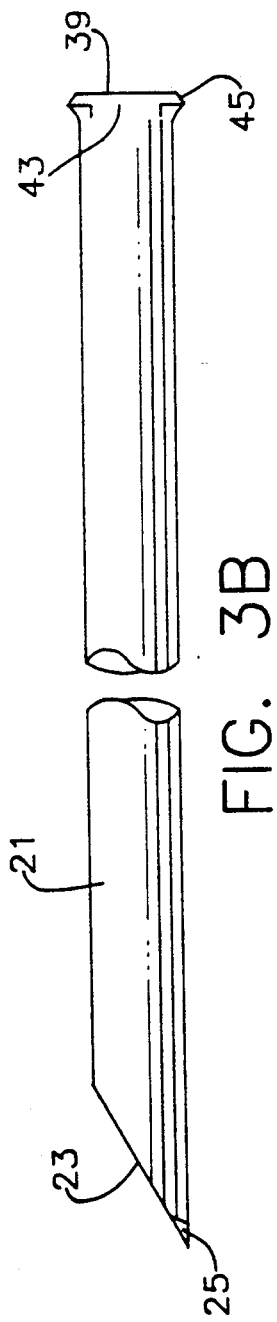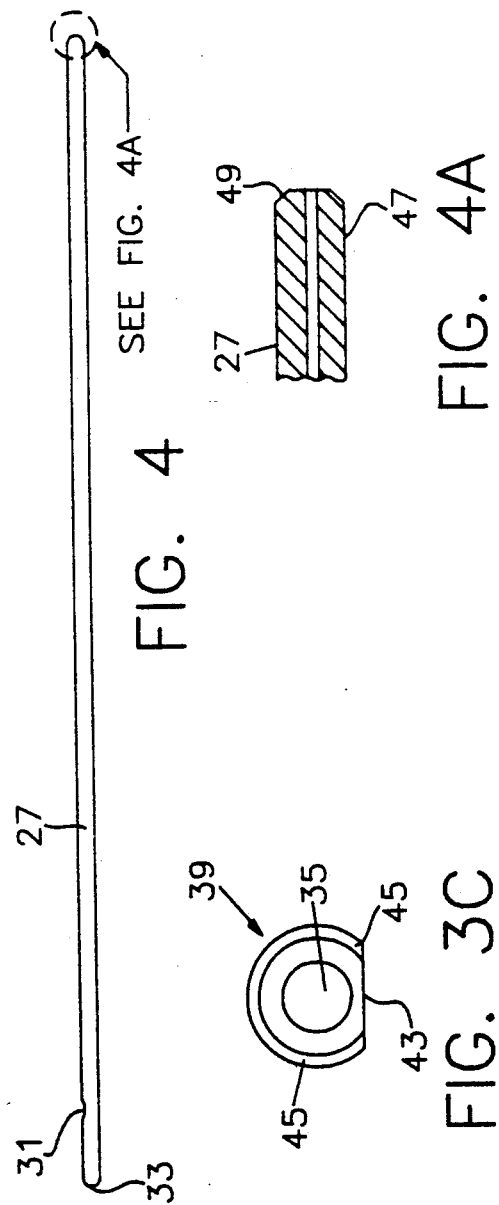

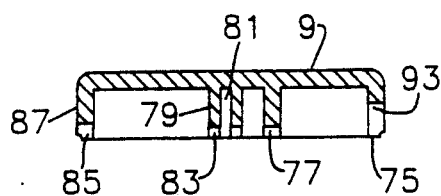
FIG. 7D
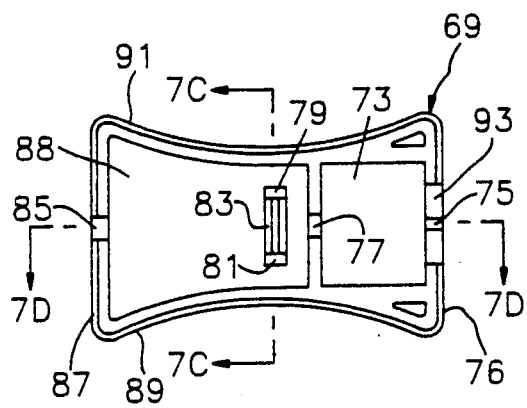 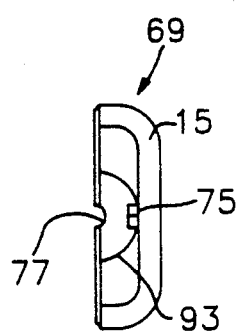 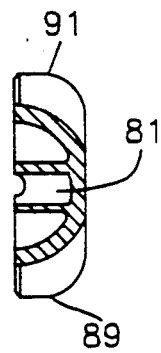
FIG. 7A   FIG. 7B   FIG. 7C
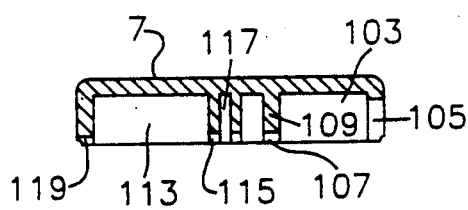
FIG. 8D
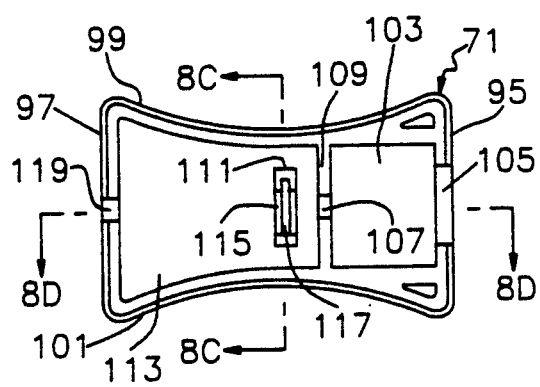 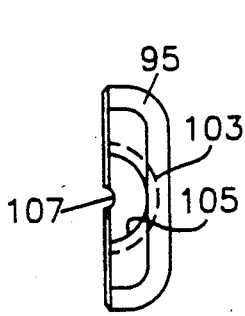 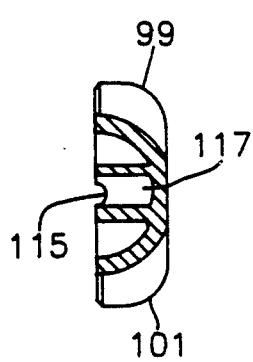
FIG. 8A   FIG. 8B   FIG. 8C

VERESS NEEDLE ASSEMBLY

FIELD OF THE INVENTION

The field of the present invention generally relates to surgical instruments, and more particularly relates to Veress needles and trocar instruments.

BACKGROUND OF THE INVENTION

In various medical procedures including endoscopic examination of a patient's abdominal cavity, and/or the draining of fluids therefrom, it is necessary that easy access be gained to the abdominal cavity. Typically, a surgical instrument known as a trocar that consists of a sharp pointed instrument, may be used to penetrate the abdominal wall to create an access hole therethrough into the abdominal cavity. Another instrument known as a Veress needle typically consists of a hollow outer needle having the end opposite the pointed end rigidly secured to a handle-like housing. A tube or hollow stylet is slidably carried within the hollow needle. One end of the tube is typically secured to one end of a piston-like hollow plunger slidably retained within a plunger cylinder formed in the handle-like housing. The other end of the plunger is typically attached to one end of a spring, the other end of which is connected to the top end of the plunger cylinder. A centrally located axially directed hole through the housing connects the interior of the plunger cylinder to a port at the end of the housing for receiving a petcock or valve mechanism. The other end of the tube typically projects beyond the needle point, with the tube having a gas exit hole through the side of the tube proximate the tip. The tube is oriented within the needle to insure that the gas exit hole of the tube is not blocked by the needle when the tubing end is protruding from the needle via the spring biasing. The free or protruding end of the hollow tube is closed off, typically via a plug.

In using such a known Veress needle, a physician pushes the free end of the tube against the abdomen of a patient. The tube retracts via the spring biasing, permitting the needle to be forced through the abdominal wall into the abdominal cavity, whereafter the free end of the inner tube pops out or extends from the needle via the spring biasing, thereby exposing the gas exit hole. This, of course, assumes that the needle is in an open area of the abdominal cavity, and is not pushing against some internal organ, which would prevent the inner tube from so popping out or moving to its extended position relative to the needle. The physician can then connect a gas line to the valve or petcock, and cause gas to enter into the Veress needle, pass through the tube and exit out of the gas exit hole of the tube into the abdominal cavity for insufflating the abdominal cavity. Alternatively, fluid can either be forced into or sucked from the abdominal cavity through use of the Veress needle.

There are many examples in the prior art of Veress needle and trocar instruments. A number of such prior instruments are discussed below.

Bauer et al., U.S. Pat. No. 4,379,458, teaches a trocar sleeve assembly that includes an interior chamber having a ball valve assembly. When a trocar is passed through the sleeve assembly, the ball valve is opened via passage of the trocar and retained in the open position so long as the trocar is present. When the trocar is removed, the ball is resiliently biased to move back into a position for closing off the trocar channel leading from the interior of the chamber to the uppermost portion of the trocar sleeve. It appears that any gases that passed through the sleeve or the trocar would by necessity have to pass over interior components, such as the ball itself, and a leaf-like spring 11 before entering the abdominal cavity.

Moll, U.S. Pat. No. 4,601,710, discloses a trocar assembly which includes a spring biased outer tubular protective shield that is extended beyond the end of the piercing tip of a trocar obturator enclosed within the shield. When the trocar is being inserted through the wall of a body cavity, the shield is forced back to its retracted position for permitting the piercing tip of the trocar to be forced through the abdominal wall, whereafter the shield then moves back over the piercing tip. A port is provided in the associated trocar assembly for permitting an insufflating gas to be injected into the port, and through the trocar tube into the abdominal cavity. However, the gas must pass through springs and other mechanical mechanism that are not easily sterilized, prior to entering the abdominal cavity.

Moll et al., U.S. Pat. No. 4,654,030, discloses a relatively complicated trocar assembly. An outer tubular member of the trocar assembly for carrying an elongated obturator, has one end that is fitted into a body member including a flap valve that locks into a slot in the trocar tube for preventing that end from moving out of the holding body. A manual pivot is provided for permitting the flap valve to be moved out of engagement with the slot of the trocar tube, for permitting release of the same. Spring biasing is provided for the trocar tube. A stopcock port 89 is included on the side of the holding body for permitting gases to be injected through the trocar tube into a body cavity.

Warring, U.S. Pat. No. 4,808,168, teaches a pneumoneedle. As shown in the exploded assembly diagram of FIG. 2, gas is injected through the stopcock 12 and must flow around an interior bias spring 13, and the outside of the stylet 14, in passing through the hollow needle 16 into a body cavity. In FIG. 5, an alternative embodiment shows gas passing through the spring chamber 32 and a hallow stylet 36, to exit from a hole 42 into the abdominal cavity. Note that a plug 40 is used to seal the leading end 38 of the lumen 39.

Adair, U.S. Pat. No. 4,869,717, discloses a disposable trocar including a removable gas insufflation needle which can be used to inflate a body cavity with an inert gas. As shown in the figures, a tubular rod 16 has an opening 22 at its forwardmost end, and is slidably mounted within a needle 10. Tubular member 16 is spring biased via a spring 24 captively retained within a lower portion of a housing 36. Any gases passing through the tube 16 must flow over the spring before entering the tube 16.

Lander, U.S. Pat. No. 4,902,280, discloses a trocar assembly that includes a leaf spring mechanism for insuring that a protective outer sheath cannot be inadvertently retracted. Other spring biasing is provided for biasing a tube 16 surrounding a stylet 14. The inner stylet is rigidly connected at one end to an interior portion of a housing.

Holmes, U.S. Pat. No. 4,931,042, teaches a trocar assembly which includes an obturator 22 enclosed in a central portion of the extended portions of the trocar assembly that appears to be a solid rod-like member having a piercing tip 24. Gases must flow over this rod or between the inner and outer walls of outer and inner sheath members. Similar to the previous patent, a leaf spring latching mechanism is included within the main housing of the trocar assembly. Also, a number of other lever-like latching mechanisms are included therein.

The present inventors observed a number of problems with prior Veress type needle assemblies. One problem is that insufflating gas passing through such prior assemblies typically must pass over springs and other mechanical mechanisms that are not easily sterilized, and could cause contaminants to flow through the tube with the gas into the abdominal cavity. Also, in certain of the prior designs undesirable pressure vessels may be created within the assembly as the gases pass through the assembly. This is especially true when the end of the tubing inserted into the abdominal cavity becomes blocked, causing gas pressure to build up within the needle assembly. Also, when such blockage may occur due to body debris, for example, the prior needle assemblies do not facilitate clearing of such debris away from the gas exit hole. Also, prior instruments do not provide any means for warning a physician that the pointed end of a Veress needle, for example, is against an abdominal wall, or an internal organ.

SUMMARY OF THE INVENTION

With the problems of the prior art in mind, one object of the present invention is to provide an improved Veress needle assembly.

Another object of the invention is to provide a Veress needle assembly in which insufflating gas passed therethrough is not exposed to multiple parts or components, for substantially minimizing the risk of contaminants being carried by the gas into the abdominal cavity.

Yet another object of the invention is to provide a Veress needle assembly with a visual indicator that the pointed end of the needle is either against the abdomen outer wall, preparatory to penetrating the abdominal wall, or that thereafter the point of the needle is against some interior body member within the abdominal cavity, thereby minimizing injury to internal organs.

Another object of the invention is to substantially minimize creation of pressure vessels within the needle assembly during the passage of gas therethrough into the abdominal cavity.

Still another object of the invention is to facilitate manual manipulation of the Veress needle assembly for clearing any body debris from the gas exit hole of the tube member.

Another object of the invention is to provide a veress needle assembly that is of simplified design, and can be easily assembled with substantially automatic orientation of the various components to one another.

In one embodiment, the present invention includes a relatively long outer needle that is rigidly retained at one end within a central portion of a housing assembly. A tube slidably retained within the needle has one end rigidly connected to a bobbin within the housing. The bobbin is captively retained within a cylindrical cavity in the housing, with the bobbin being spring biased in the axial direction. The opposite end of the housing includes port means for connection to a petcock or valve for receiving insufflating gas for passage directly from an interior cavity of the bobbin into the tube. The free end of the hollow tube is closed off, and a gas exit hole is located through a side wall of the tube proximate its free end. Indexing means are included for insuring that the gas exit hole is always free of the needle when the tube is in its extended position from the needle. Indicating means for providing a visual indication to the surgeon that the tube is retracted and the needle is against either the outer wall of the abdomen or is against some internal organ, is provided via one end of the bobbin partially extending from the end of the housing whenever the tube retracts.

In another embodiment of the invention, debris can be cleared from the gas exit hole of the tube by means permitting the bobbin and tube to be manually moved for repetitively retracting and extending the tube in a manner causing the gas exit hole to wiped against an edge of the needle point.

BRIEF DESCRIPTION OF THE DRAWINGS

The various embodiments of the invention are described in detail below with reference to the drawings in which like items are indicated by the same reference designation, wherein:

FIG. 1 is a pictorial view of one embodiment of the invention showing the cannula or small tube in its extended position from an outer needle;

FIG. 1A is an enlarged detailed view of the portion of the embodiment of FIG. 1 showing the tube in its extended position from the needle;

FIG. 2 is a pictorial view of the one embodiment of the invention with the tube in its retracted position within the needle, whereby a colored bobbin is caused to extend from the end of a finger housing for visually indicating such retraction of the tube within the needle;

FIG. 2A is an enlarged detailed view of the needle tip portion of FIG. 2, showing the inner tube in its retracted position therein;

FIG. 3A is a top view of the needle along its longitudinal axis for one embodiment of the invention;

FIG. 3B is a side view of the needle of one embodiment of the invention taken along the longitudinal axis thereof;

FIG. 3C shows an end view of the needle of FIG. 3A looking in the direction 3C—3C;

FIG. 4 is a side elevational view of the tube of one embodiment of the invention;

FIG. 4A is an enlarged detailed view of the longitudinal cross section of the tube of FIG. 4, at the end of the tube where it is inserted into a bobbin of FIG. 5, in one embodiment of the invention;

FIG. 7A is a top view of the interior of a lower half of a housing of one embodiment of the invention;

FIG. 7B is an elevational view of the right side end of the housing of FIG. 7A;

FIG. 7C is a sectional view of the housing taken along 7C—7C of FIG. 7A;

FIG. 7D is a cross section taken along 7D—7D of the lower housing of FIG. 7A;

FIG. 8A is a top inside view of the interior of an upper half of a housing of one embodiment of the invention;

FIG. 8B is an end elevational view looking from the right relative to the upper housing of FIG. 8A;

FIG. 8C is a sectional view taken along 8C—8C of FIG. 8A;

FIG. 8D is a sectional view taken along 8D—8D of the upper housing of FIG. 8A;

DESCRIPTION OF THE PREFERRED EMBODIMENTS OF THE INVENTION

Figure 5:
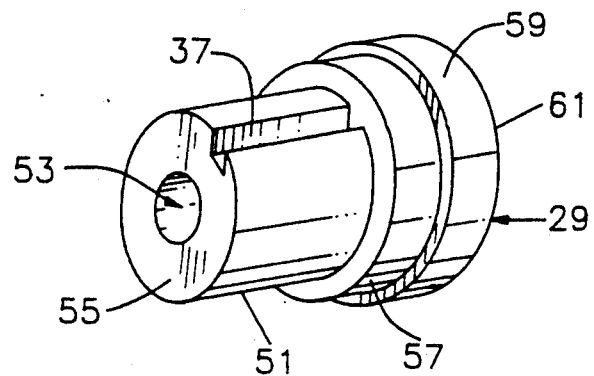
FIG. 5 is a pictorial view of a bobbin of one embodiment of the invention.

As shown in FIG. 1, a Veress needle assembly of one embodiment of the invention includes a relatively elongated housing with arcuate-like side portions 3, 5, substantially flat top and bottom surfaces 7, 9, respectively, and substantially flat end portions 13 and 15. The sides 3 and 5 of housing 1 are substantially rounded in their centralmost portions, and tend to become progressively less rounded proceeding from the center thereof towards the ends of the housing 1. The corners of the housing 1 are provided with a radius, in the preferred embodiment. A petcock 17 is connected to an inlet port 19 (see FIG. 2) at the top end 15 of housing 1. A hollow needle 21 is rigidly retained at one end within the housing 1, and has a major portion extending from housing 1 that terminates at its other end 23 to form a tapered point 25. A cannula or hollow relatively small diameter tube 27 is slidably mounted within needle 21. One end of the tube 27 is rigidly secured within housing 1, as will be described below.

As will be described in greater detail below, the one end of the tubing 27 is secured to an end of a bobbin 29 (see FIG. 9) in a manner permitting the tubing 27 to move within needle 21 along the longitudinal axis thereof and of housing 1. In a rest or normal position the tube 27 protrudes with its other end away from the pointed end 25 of needle 21, as shown in FIG. 1A. With tubing 27 in its extended position as shown in FIG. 1A, a gas exit hole 31 through a portion of the side wall of tube 27 is unobstructably exposed as shown in FIG. 1A. Note that the gas exit hole 31 is located near the tip 33 of tube 27. Note that in the preferred embodiment, the gas exit hole 31 is aligned for being centered with the maximum longitudinal axis of the needle 21, and oriented to be centered with the exit hole 35 of the needle 21 to the maximum extent for avoiding any portion of the needle 21 from blocking the hole 31 when the tube 27 or stylet 27 is in its extended position protruding outward from needle 22. As will be explained later in detail, note also that the hole 31 is also aligned with the longitudinal axis of a keyway of slot 37 of a bobbin 29 (see FIGS. 2 and 5).

If, for example, a physician grasped the housing 1 in his fingers along the arcuate side portions 3 and 5, the Veress needle assembly can be manipulated in a manner similar to throwing a dart. When the present assembly is located preparatory to penetrating the wall of a patient's abdomen, the tip 33 of the tube 27 is placed against the outer wall of the abdomen at the spot to be penetrated, and the housing 1 is moved toward the abdomen, whereby the spring biased tube is pushed to a retracted position in needle 21, as shown in FIG. 2A. With the tube 27 in its retracted position, this causes an end portion of the bobbin 29 to protrude from the back of the housing 1, and serves as a visual indication to the physician that the tube 27 is in its retracted position, and the short tip of the needle 25 is bearing against a relatively solid surface (in this example, the outer wall of a patient's abdomen). The physician may now proceed to first insure that the needle is properly aligned, whereafter the physician forcefully pushes the housing 1 toward the abdomen for forcing the needle 21 to penetrate through the abdominal wall and into the abdominal cavity of the patient. Once the abdominal cavity is so penetrated, the tube 27 will pop out of the needle 21 via the spring biasing to the extended position shown in FIG. 1A. The physician will have a visual indication that this has occurred by observing the end of the bobbin 29, which will be flush with the end of the housing 1 if the tube 27 has returned to its extended position. To aid in this visual indicator mechanism of the present invention, the indicator end of the bobbin 29 is given a prominent color such as red, for example. It is important to also note that this visual indicator feature of the present invention is also useful to a physician for noting whether, after penetrating the abdominal cavity, the free ends of the needle and tube are away from internal organs. If the needle 21 happens to be inadvertently pushed against an internal organ, the tube 27 will be pushed back to its retracted position, causing the bobbin end 29 to again protrude from the end of the housing 1, alerting the physician to change the orientation of the Veress needle assembly to avoid such contact with an organ.

Another advantage of the visual indicator feature of the present invention is that it is useful in assisting a physician to clear debris away from the gas exit hole 31 of tube 27, if the hole should become clogged with debris during the passage of insufflating gas through the tube 27 into the abdominal cavity. To clear hole 31 of debris, the physician without removing the Veress needle assembly from the abdominal cavity, would merely grasp the housing 1 in the fingers of one hand, and with the fingers of the other hand pull the petcock 17 back to retract the tube 27 into needle 21, while watching the bobbin end showing that the tube 27 is retracted. Immediately thereafter, the physician would release the petcock 17 for permitting the spring biasing of the bobbin 29 to cause the tube 27 to return to its extended position. This debris clearing operation can be repeated rapidly a necessary number of times for clearing hole 31 of such debris. In the preferred embodiment, as will be described in greater detail below, the dimensioning between the inside diameter of the needle 21 and outside diameter of the tube 27 is such that when the tube 27 is moved towards its retracted position, the inside edge of the needle point hole 35 serves to wipe against the edges of the gas exit hole 31 of tube 27, with this wiping action being repeated when the tube 27 next moves outward and away from needle 21 to its extended position, as previously described. This wiping action greatly assists in clearing debris from the hole 31 by reciprocal movement of tube 27 as previously described.

Greater details of the design of the preferred embodiments of the present Veress needle assembly will now be described. As shown in FIG. 3A, the needle 21 at one end 23 is tapered to a sharpened point 25. The other end 39 of needle 21 includes a flared circumferential portion 41. The flair 41 is ground away to form a portion tangent to the outside diameter of needle 21 at tangent portion 43. The side view of needle 21 of FIG. 3B shows the tangent portion 43. Note also that the flared portion 41, in this example, consists of a 45° flare. Also note that the edge of the flared portion has a chamfer or beveled edge 45. Note also the end 39 of needle 21, showing a chamfered edge 45. Also note that in one engineering prototype of the invention, the needle 21 was fabricated from 13 gage stainless steel having an outside diameter of 0.095 inch, and an inside diameter of 0.071 inch, for example. Also, the needle was 5.28 inches in length along its maximum longitudinal axis.

In FIG. 4, the tube 27 is hollow, and includes a sealed off tip 33. The other end of the tube 27 is chamfered or beveled as shown in the longitudinal detailed cross sectional view of FIG. 4A. In an engineering prototype, the tube 27 was fabricated from 16 gage stainless steel having an outside diameter of 0.065 inch and an inside diameter of 0.047 inch. The hole 31 was located about 0.151 inch from the tip 33, and at a radius of 0.031 inch. Also, the tip 33 was sealed via a spin weld operation, and polished to provide a full radius. It is important to note that in the preferred embodiment such spin weld closure is used to avoid the use of separate plugs as in the prior art. In this manner, the possibility of such a plug coming loose and falling into an abdominal cavity is completely avoided.

A pictorial of the bobbin 29 is shown in FIG. 5. The bobbin 29 is generally cylindrical in shape, and includes a dowel-like rear or back portion 51 having a centrally located bore or through hole 53, a back face or rear face 55, with the keyway or indexing slot 37 formed from a longitudinal cutout partially into a portion of the sidewall of the dowel-like rear portion 51. In this example, the keyway 37 is formed from an elongated rectangular slot, as shown. The inner end of the dowel-like portion 51 terminates at and is concentric with a relatively short band-like cylindrical portion 57, with the other end of the latter terminating at and being concentric with an even narrower cylindrical-like portion 59 of greater outside diameter than section 57. The face 61 of section 59 provides the front face 61 of the bobbin 29 (see FIG. 6C). Accordingly, in this example, a two-step bobbin 29 is thus formed, with the first step being the side wall or outer circumference of section 57, and the second step being the side wall or outer circumferential surface of section 51.

Figure 6A:
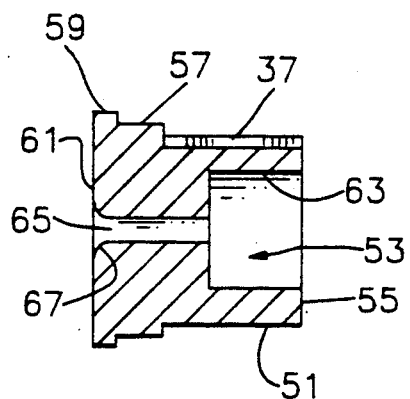
FIG. 6A is a cross section of the bobbin of FIG. 5 taken along the central longitudinal axis thereof bisecting a keyway slot.
Figure 6B:
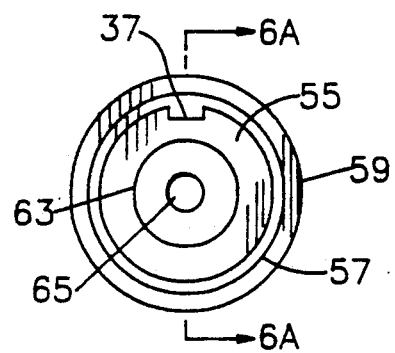
FIG. 6B is an elevational end view taken from the left relative to FIG. 5.
Figure 6C:
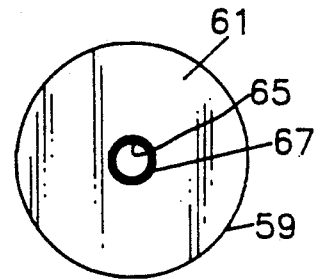
FIG. 6C is an elevational view of the opposite end of the bobbin relative to FIG. 5.

In FIG. 6A a longitudinal cross-sectional view bisecting the keyway or slot 37 and bore 53 of bobbin 29 is shown. As shown, the bore 53 includes two portions, a porthole portion 63 of relatively large inside diameter that terminates less than midway into the rear of dowel-like portion 51 to a centrally located through hole 65 of relatively smaller inside diameter than that of porthole 63. Note that the through hole 65 is slightly counterbored at its exit from the front face 61 for forming a narrow chamfer portion 67 to assist in receiving the end 47 of tube 27 during the assembly process to be described below (see FIG. 9). The front face of the bobbin is shown in FIG. 6C.

In this example, the bobbin 29 is fabricated from a single piece of Lexan (trademark of General Electric Co.), part No. HP1, which is of a red color, for enhancing the visual indicator function provided by the bobbin 29, as previously described. Also, in the engineering prototype, the bobbin had a length of 0.5 inch, a width of 0.06 inch for cylindrical portion 59, 0.10 inch for the width of cylindrical portion 57, and a length of 0.34 inch for cylindrical or dowel-like portion 51. The slot or keyway 37 has a width of 0.75 inch, and a depth of 0.065 inch. The through hole 65 has a diameter of about 0.063 inch, the porthole 63 a diameter of about 0.185 inch, the diameter of the rear face 55 being about 0.35 inch, of the front face 61 being about 0.47 inch, and the outside diameter of the first step or cylindrical section 57 being about 0.40 inch. Note that these and any other dimensions given herein relative to the prototype design, are given for purposes of illustration only, and are not meant to be limiting in any manner. With further reference to the prototype design, the bobbin 29 has a length or depth of about 0.188 inch for the porthole 63, and a length of about 0.312 inch for the through hole 65.

The housing 1 is, in this example, fabricated from two half sections consisting of a lower housing section 69, and an upper housing section 71, as shown in FIGS. 7A and 8A, respectively. With further reference to FIG. 7A, the lower housing section 69 includes in its interior portion a semicircular cavity 73 for receiving bobbin 29; an indexing tab or key 75 for locking into keyway 37 of bobbin 29 for preventing rotation of the latter and properly orienting the same during assembly; a semicircular cradle-like portion 77 for receiving a portion of tube 27; a cavity 88 including a pedestal-member 79 having a semicircular centrally located transverse slot 81 and a semicircular cradle-portion 83 for receiving one-half of the flared end portion 41 of needle 21; a centrally located semicircular cutout or cradle 85 in its front or left edge 87, with cradle 85 serving to support a portion of needle 21; and arcuate sidewall portions 89 and 91. Note that all of the corners on the lower housing 69 are rounded or have a radius, as are all edges. The top end 15 of the lower housing 69 is shown in FIG. 7B. A semicircular recess 93 is centrally located in the top inside edge of lower housing section 69, as shown. The key or locking tab 75 is located in the center of the ar edge formed by recess 93 for receiving a portion of cylindrical member 51 of bobbin 29. FIG. 7C shows a cross section of lower housing section 69 taken along 7C—7C of FIG. 7A. A longitudinal cross-sectional view taken along 7D—7D of lower housing section 69 in FIG. 7A is shown in FIG. 7D.

The other half of the housing is shown as upper housing section 71 in FIG. 8A. As shown, the upper housing section 71 is substantially similar to the lower housing section 69. The upper housing section 71 includes a top end 95; bottom end 97; arcuate sides 99 and 101; a cavity 103 for receiving a portion of the bobbin; a semicircular cutout 105 in the central portion of the edge of the top 95 for receiving and supporting an end portion of cylindrical section 51 of bobbin 29; a semicircular cutout 107 in a transverse rib 109 for supporting a portion of tube 27; a pedestal-like support member 111 protruding upward from the floor of a bell shaped cavity 113; a semicircular centrally located cutout 115 in pedestal 111; a slotway 117 transversely cut through the semicircular cutout portion 115 along the longitudinal axis of pedestal 111; and a semicircular cutout portion 119 centrally located in the edge of the bottom end 97. The semicircular cutout 119 provides a support cradle for a portion of the outside wall of needle 21 passing into the housing section 71. The pedestal 111 with its semicircular cutout 115 and slotway 117 is positioned for receiving the other half of the flared end portion 41 of needle 21, and the tangent portion 43 provided across a portion of the flared portion 41. An end view of the top surface 95 is shown in FIG. 8B. A transverse cross-sectional view taken along 8C—8C of FIG. 8A is shown in FIG. 8C. A longitudinal cross-sectional view taken along 8D—8D of upper housing Section 71 in FIG. 8A is shown in FIG. 8D.

In this example, the upper housing section 71 and lower housing section 69 are each fabricated from Lexan (trademark of General Electric Co.) part No. HP1, of a selected color such as white. Each section 69 and 71 can be fabricated in one piece. Also in this example, the housing half section 69 and 71 are each one and one-half inches long.

Figure 9:
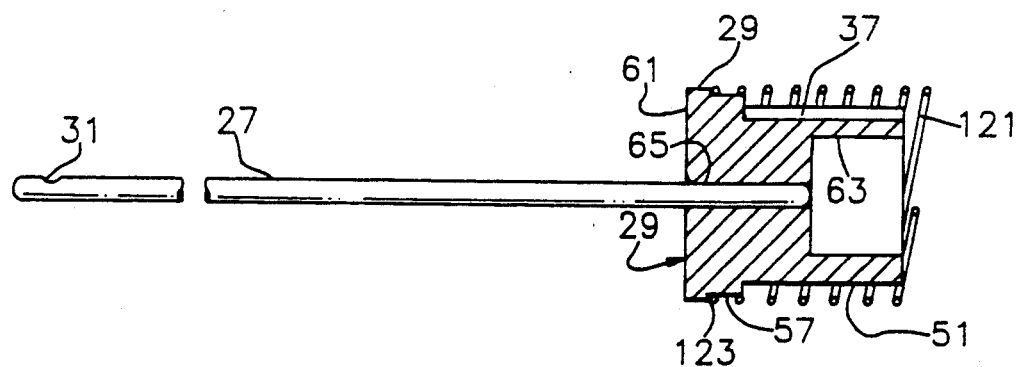
FIG. 9 is a subassembly view of one embodiment of the invention showing the tubing inserted into the bobbin, with the bobbin shown in longitudinal cross section, and with a spring attached to the bobbin.

The first step in assembling the Veress needle assembly of the present invention is to pres fit the end 47 of tube 27 into through hole 65 of bobbin 29 as shown in FIG. 9. A spring 121 is mounted at one end onto step 57 of bobbin 29. At this end, the spring bears against the shoulder 123 of bobbin 29, and after complete assembly of the present Veress needle, the other end of spring 121 will bear against the inside wall of the top end of housing 1, as will be better illustrated below. Note that through use of the two-step bobbin 29, the spring 121 is substantially prevented from rubbing against the lowermost step portion 51 of bobbin 29, or against the internal walls of cavities 73 and 103 of housing sections 69 and 71, respectively.

Figure 10:
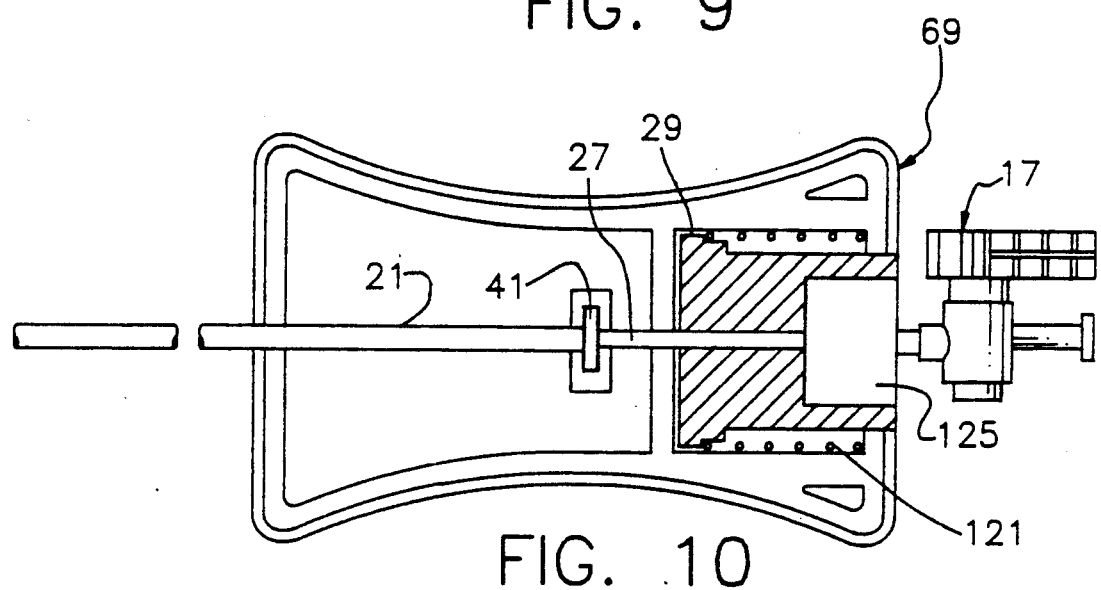
FIG. 10 is a subassembly view showing the needle, tube, bushing, spring, and a petcock assembled into one housing half of one embodiment of the invention.

A very important design feature of the present invention is that the tube 27 is press fit into bobbin 29 with its end portion 47 forced all the way through passageway 65 to the porthole 63. Note that tube 27 is oriented to insure exit hole 31 is in the same vertical plane as keyway or slot 37 of bobbin 29, and opens toward the same horizontal plane as slot 37. In this manner, when the petcock 17, in this example, has its outlet 125 forced into porthole 63 up to passageway 65, as shown in FIG. 10, any gases passing from the petcock 17 into the tube 27 flow directly from the petcock to tube 27, thereby substantially reducing contamination of the gas by eliminating the need for having the gas flow over other components as it travels through the present Veress needle assembly. In addition, also in this manner, the formation of pressure vessels within the Veress needle assembly is substantially eliminated.

As shown in FIG. 10, the next step is to join the petcock 17 to the subassembly of FIG. 9 by either press fitting the petcock outlet 125 into the porthole 63, or ultrasonically welding the same together, or adhesively fixing the same together, or in some other way insuring that a gas-tight rigid connection is formed therebetween. The flared end 41 of needle 21 is then slid over tube 27, and the subassembly of needle 21, tube 27, bobbin 29, spring 121, and petcock 17, in this example, is mounted into the lower housing section 69 as shown in FIG. 10. The keyway 37 of bobbin 29 is locked into the key 75 by rotating the bobbin 29 to properly orient it with tube 27. Also, the needle 41 is properly oriented or indexed via the tangent portion 43 of flared portion 41 (see FIG. 11). A useful assembly fixture would be a relatively elongated rectangular block having a cavity or recess shaped for securely receiving a lower portion of the lower housing section 69 for holding this section in place during the assembly process.

Figure 11:
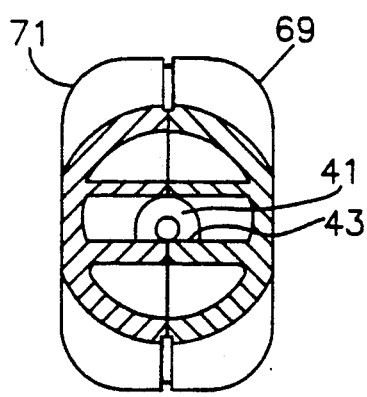
FIG. 11 is a partial cross-sectional view taken along 11—11 of FIG. 1, showing the retention of the needle within its cradle in a configuration preventing rotation of the needle and indexing it into a desired position.

After the subassembly shown in FIG. 10 is completed, the upper housing section 71 is placed over the lower housing section 69 and rigidly connected thereto by using conventional techniques such as ultrasonic welding, or gluing together through use of an appropriate adhesive, or mechanical fasteners, and so forth. When the two housing sections 69 and 71 are so mated together, the needle 21 will be prevented from rotating as shown in FIG. 11 for the cross section 11—11 of FIG. 1. By orienting the gas exit hole 31 of tube 27 to lie in the same vertical plane as the keyway or slot 37 of bobbin 29, with the gas exit hole 31 also opening upward in the same orientation as the opening of the keyway or slot 37, in conjunction with the indexing of needle 21 as previously described, during assembly of the present Veress needle assembly, the needle 21 and tube 27 are automatically oriented and indexed to insure that the gas exit hole 31 is centered with the maximum longitudinal portion of the pointed end 25 of needle 22 as shown in FIG. 1A.

Figure 13A:
FIGS. 13A and 13B show side and end views, respectively, of a spring of one embodiment of the invention.
Figure 13B:
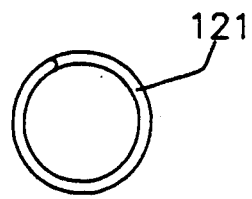

Note that the spring 121 is a conventional helical spring as shown in FIG. 13A. An end view of spring 121 is shown in FIG. 13B. In the prototype design the spring is fabricated from type T302 stainless steel, has squared ends, a force of about 6.0 grams, a maximum outside diameter of 0.460 inch, a minimum inside diameter of 0.40 inch, with six and one-half coils, a free length of about 0.625 inch, and squared ends.

Figure 12:
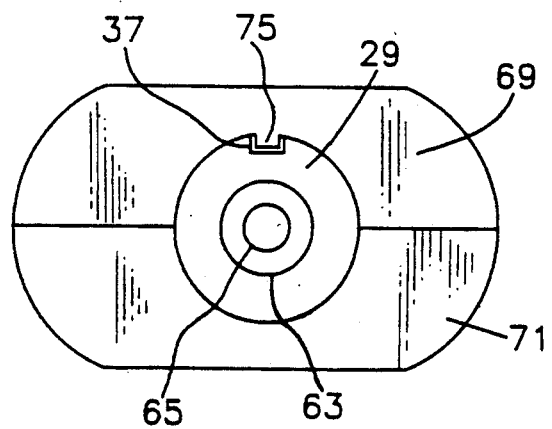
FIG. 12 is an end elevational view showing the end of the housing halves as assembled with the bobbin.

The top end view of the housing halves 69 and 71 as assembled with bobbin 29 is shown in FIG. 12. The antirotation means for preventing bobbin 29 from rotating, to in turn prevent the insufflation port or gas exit hole 31 at the end of tube 27 from rotating and being blocked by an inside wall of needle 21, is clearly shown to include the key or locking tab 25 positioned in the keyway or slot 37 of bushing 29. Note that an alternative antirotation embodiment would be to use a "D" indexing configuration between bobbin 29 and housing 1 to prevent rotation of bobbin 29. However, such a "D" antirotation configuration would cause rotational torques that would tend to separate the housing halves 69 and 71, making such an embodiment less preferred than the antirotation embodiment illustrated herein.

Figure 14:
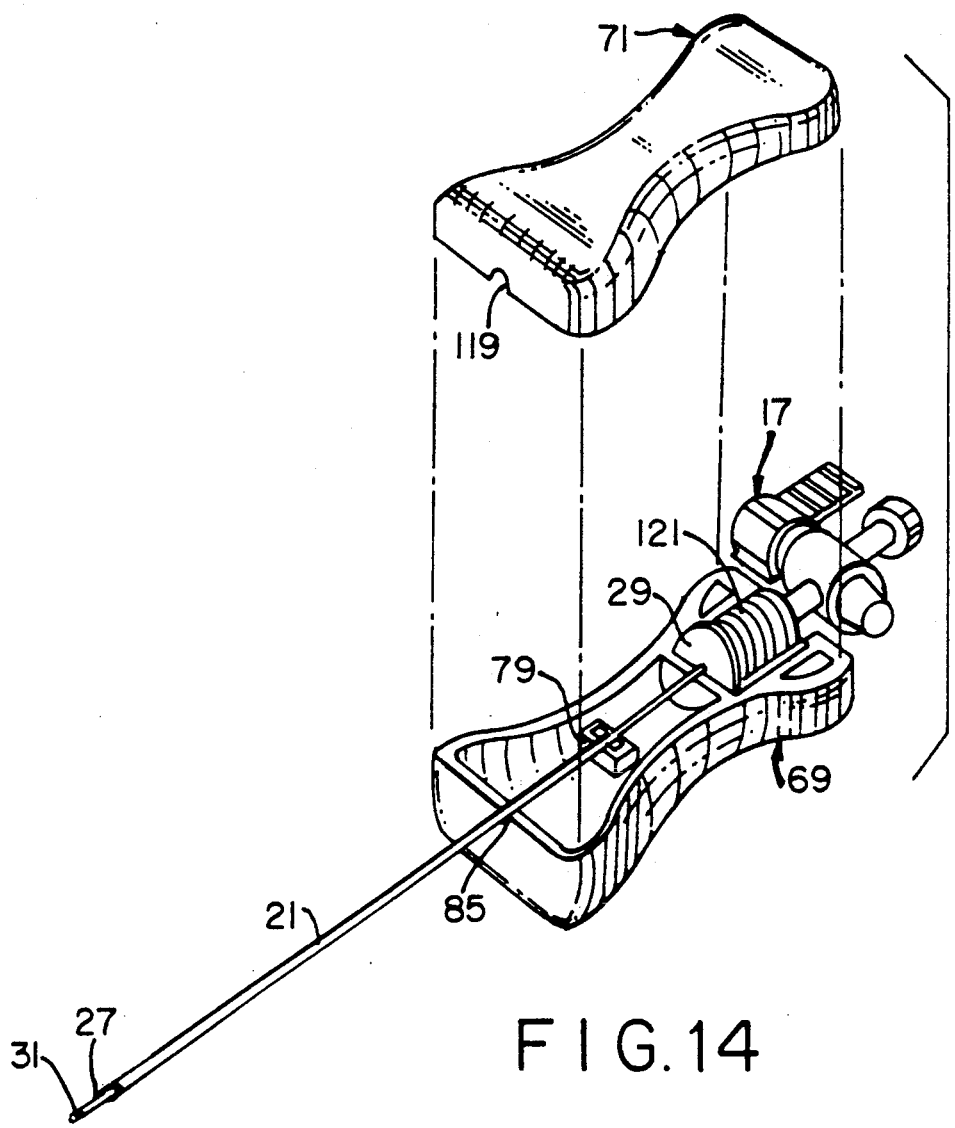
FIG. 14 is an exploded assembly pictorial of one embodiment of the invention showing the final assembly step of mating the upper housing section to the lower housing section, with the needle, tube and bobbin subassembly, and petcock in place.

In FIG. 14, an exploded assembly diagram is shown of the final assembly step for mating upper housing section 71 to lower housing section 69, with the needle 21, tube 27, and bobbin 29 assembly in place in lower housing 69. As previously described, all of the components are directly aligned at this final assembly stage.

Although various embodiments of the invention have been shown and described herein for purposes of illustration, those of skill in the art may recognize modifications to the same. Any such modifications are meant to be included in the spirit and scope of the appended claims. One such modification, for example, would be to use a "D" antirotation configuration between bobbin 29 and housing 1, as previously described. Another modification would be to leave the end of tube 27 open where it normally extends away from needle 21, and eliminate side hole 31.

What is claimed is:

1. A Veress needle instrument comprising:
a housing shaped to provide a handle;

a hollow needle having one end rigidly secured within a lowermost portion of said housing, an elongated portion of said needle protruding from a bottom end of said housing, said elongated portion terminating at a pointed another end of said needle;

a tube slidably mounted within said needle, one end of said tube normally extending out of and away from the pointed end of said needle;

spring biased fluid transfer means mounted in a topmost portion of said housing for movement within a range along the longitudinal axis of said housing, said fluid transfer means including an axial passageway therethrough having one end portion adapted for receiving and securing the other end of said tube, and having another end portion adapted for receiving a fluid coupling through a hole in the top end of said housing, for directly passing fluid from said fluid coupling to said tube, said fluid transfer means being normally biased to a rest position for placing said tube in its normally extended state; and visual indicator means connected to said fluid transfer means, for providing a visual indication at said housing for indicating when a force imparted on the one end of said tube overcomes the spring biasing on said fluid transfer means causing it to move toward the top end of said housing with said tube retracting into said needle.

2. The Veress needle instrument of claim 1, wherein said fluid transfer means includes:

a spring biased bobbin having a central passageway at a front end portion for receiving and rigidly securing the other end of said tube, said central passageway opening into a porthole in a back end portion of said bobbin for receiving said valve or fluid coupling.

3. The Veress needle instrument of claim 2, wherein said visual indicator means includes a rearmost portion of said bobbin that is adapted to protrude out of said hole in the top end of said housing, whenever said tube retracts into said needle, said rearmost portion of said bobbin being substantially wholly within said housing whenever said tubing is in its normally extended position relative to said needle.

4. The Veress needle instrument of claim 3, wherein said bobbin consists of a two-step configuration having a frontmost disk-like relatively narrow cylindrical portion providing a front face, said frontmost portion stepping down to slightly wider interior disk-like portion of slightly smaller outside diameter than said frontmost portion, said frontmost portion providing a circular shoulder juxtaposed to said interior portion, said interior portion stepping down to a relatively long dowel-like rearmost portion of lesser outside diameter than said interior portion, said rearmost portion providing a rear face for said bobbin, and wholly containing said porthole extending from the rear face partially into said rearmost portion.

5. The Veress needle instrument of claim 4, wherein the one end of said tube is sealed off, and a small hole through a side wall of said tube is located proximate its one end.

6. The Veress needle instrument of claim 5, further including first antirotation means for preventing said bobbin from rotating within said housing.

7. The Veress needle instrument of claim 6, wherein said first antirotation means includes:

an open elongated slot in an outside wall of said rearmost portion of said bobbin, said slot being aligned with the longitudinal axis of said bobbin; and an indexing tab protruding upward from a circumferential edge of said hole through the top end of said housing, said indexing tab being locked captively into the slot in the rearmost portion of said bobbin;

said tube being oriented in said bobbin for insuring that said side hole in said tube is substantially clear of any blockage by an interior wall portion of said needle, whenever said tube is in its extended position relative to said needle.

8. The Veress needle instrument of claim 7, further including second antirotation means for preventing said hollow needle from rotating within said housing.

9. The Veress needle instrument of claim 7, wherein said second antirotation means includes:

said hollow needle having its one end flared with a tangent portion along the circumference thereof; and a mounting cradle located in said housing below the topmost portion of said housing for receiving said flared end of said needle with the tangent portion rigidly abutted against a flat mounting surface of said cradle, and with the remaining portion of said flared end being retained in a truncated circular cavity, said needle being aligned with the longitudinal axis of said housing.

10. The Veress needle instrument of claim 9, further including means for automatically aligning said tube and needle during assembly of said instrument, for insuring that the side hole in said tube in its extended position relative to said needle is substantially clear of any blockage by an interior wall portion of said needle.

11. The Veress needle instrument of claim 10, wherein said automatic alignment means includes:

said tube positioned in said bobbin with said side hole of said tube being in the same vertical plane as the slot of said bobbin and opening toward the same horizontal plane as the slot; and the positioning of said indexing tab along the circumferential edge of said hole at the top end of said housing, the orientation of the truncated circular cavity of said mounting cradle all being predetermined relative to a subassembly of said tube and said bobbin, and the orientation of the pointed end of said needle to the tangent surface on the flared end of said needle, for insuring automatic alignment of said needle to said tube upon assembly of said instrument.

12. The Veress needle instrument of claim 9, wherein said housing includes:

a first cavity in its frontmost portion for receiving said bobbin; and a second cavity in the bottommost portion of said housing including said mounting cradle 13. The Veress needle instrument of claim 12, further including:

a spring for providing the spring biasing of said bobbin, said spring being mounted over the interior and rearmost portions of said bobbin, one end of said spring being secured to the interior portion and abutting against the shoulder formed by said frontmost portion, the other end of said spring abutting against an inside wall of the top end of said housing, said spring biasing said bobbin to move toward the bottom end of said housing, said bobbin being movable between top and bottom end walls of said first cavity.

14. The Veress needle instrument of claim 2, further including a petcock having a fluid outlet rigidly secured into said porthole of said bobbin.

15. The Veress needle instrument of claim 1, wherein the other end of said tube is inserted through the central passageway of said bobbin for opening directly into said porthole of said bobbin.

16. The Veress needle instrument of claim 1, wherein said hollow needle and said tube each consist of stainless steel.

17. The Veress needle instrument of claim 2, wherein said bobbin and said housing each consist of plastic material.

18. The Veress needle instrument of claim 1, wherein said housing consists of a configuration having substantially flat top and bottom surfaces, substantially flat top and bottom ends, and arcuate sides that are substantially rounded in their respective center portions and become progressively flatter toward the ends.

19. The Veress needle instrument of claim 5, wherein the outside diameter of said tube and the inside diameter of said needle are dimensioned for causing an inside edge of the open pointed end of said needle to provide a wiping action against the outer circumference of said side wall hole near the one end of said tube, whereby when said tube is reciprocally moved between its extended and retracted positions relative to said needle debris about said side wall hole of said tube is removed therefrom.

20. A Veress needle instrument comprising:
a housing shaped to provide a handle;
a hollow needle having one end rigidly secured within said housing, an elongated portion of said needle protruding from a bottom end of said housing, said elongated portion terminating at a pointed another end of said needle;
a tube slidably mounted within said needle, one end of said tube being sealed off and normally extending out of and away from the pointed end of said needle, a small gas exit hole being located proximate said one end of said tube through a side wall thereof;
a spring biased bobbin mounted in a topmost portion of said housing for movement within a range along the longitudinal axis of said housing, said bobbin including a first central passageway at one end for receiving and rigidly securing the other end of said tube, said first central passageway of said bobbin opening into a porthole in the other end of said bobbin for receiving a valve or fluid coupling through a hole in the top end of said housing, said bobbin being normally biased to a rest position for placing said tube in its normally extended state; and
visual indicator means observable at said handle and connected to said bobbin, for visually indicating when a force imparted on the one end of said tube overcomes the spring biasing on said bobbin and moves said tube and bobbin toward the top end of said housing, whereby the one end of said tube retracts into said needle.

21. A Veress needle instrument comprising:
a housing shaped to provide a handle having a bottom end, a top end, a top surface, a bottom surface and opposing sides;
a spring biased bobbin mounted within said housing proximate the top end thereof, said bobbin being adapted for movement within a range along the longitudinal axis of said housing, said bobbin being biased in its rest position to be wholly within said housing, said bobbin being moveable away from said bottom end of said housing with a rearmost portion of said bobbin serving as a visual indicator protruding out of a hole in the top end of said housing, whenever the force of said spring biasing is overcome;
a hollow needle having one end portion rigidly mounted in said housing along the longitudinal axis thereof, and a pointed other end;
a tube slidably mounted within said needle, said tube having one end secured to and passing through a centrally located bore hole of said bobbin and opening into a porthole within an end of said bobbin proximate the top end of said housing, the other end of said tube protruding away from the pointed end of said needle with said bobbin in its rest position, the other end of said tube being sealed off, the side wall of said tube proximate its other end having a hole therethrough, whereby whenever said instrument is moved in a direction causing the tip of said tube to move against an object imparting a force overcoming the spring biasing of said bobbin, said tube retracts into said needle, causing said bobbin to move toward the top end of said housing, with the rearmost portion of said bobbin protruding out of the top end of said housing for visually indicating that said tube is retracted into said needle due to encountering some obstruction.

22. A Veress needle instrument comprising:
a housing shaped to provide an elongated handle having opposing arcuate side members permitting finger grasping, opposing bottom and top ends, and opposing front and rear surfaces, said housing further including a first interior cavity near its top end, and a second interior cavity below said first cavity and extending proximate said bottom end;
a bobbin captively and slidably mounted within said first cavity for movement therein along the longitudinal axis of said housing, said bobbin having a rear body portion dimensioned to protrude from a hole in the top end of said housing whenever said bobbin slides toward the top end, said bobbin further having a bored out axial portion of relatively large inside diameter forming a porthole proximate a rear face, and extending inward to open into a through hole of relatively small inside diameter that exits from the center of a rear face of said bobbin, said bobbin further being configured as a two-step cylindrical-like bobbin having a frontmost disk-like relatively narrow cylindrical portion providing a front face, said frontmost portion stepping down to slightly wider interior disk-like portion of slightly smaller outside diameter than said frontmost portion, said frontmost portion providing a circular shoulder juxtafaced to said interior portion, said interior portion stepping down to relatively long dowel-like rearmost portion of lesser outside diameter than said interior portion, said rearmost portion providing said rear face and wholly containing said porthole, said rearmost portion including a keyway or open slot in its outside wall aligned with its longitudinal axis;
an indexing tab or key being provided along a portion of the circumference of the hole in the top end of said housing through which said rearmost portion of said bobbin can protrude, said indexing tab being locked into the keyway or slot of said bobbin to prevent rotation of bobbin within said housing;

a needle end support being located in said second cavity near the center of said housing;

a hollow needle having a pointed end for penetrating an abdominal wall, and a flared opposite end having a tangent portion;

said needle end support including a substantially circular recess having a tangent or flat portion for receiving the flat portion of said flared needle end, and securing said needle in said housing in a manner preventing rotation of said needle and indexing said needle into proper orientation;

a tube slidably mounted within said needle, with one end of said tube passing through said needle and being rigidly secured within the length of the through hole of said bobbin, said one end of said tube thereby opening directly into said porthole of said bobbin, the other end of said tube being sealed, said tube having a relatively small exit hole through a side wall portion proximate its other end, the length and alignment of said tube relative to said needle being configured for having its other end protrude slightly away from the pointed end of said needle, with the exit hole of said tube being substantially completely clear of any blockage by an interior wall portion of said needle, whenever said bobbin is wholly within said first cavity; and a spring mounted over the interior and rearmost portions of said bobbin, an end of said spring being secured to the interior portion and abutting against the shoulder formed by said frontmost portion, another end of said spring abutting against an inside wall of the top end of said housing, said spring biasing said bobbin to be moved toward the bottom end of said housing and wholly within said second cavity, whereby if the other end of said tube engages a surface resisting the movement of said instrument toward the surface, said tube retracts into said needle, causing the pointed end of said needle to contact said surface, and said bobbin to move away from said first cavity, whereby the rearmost portion of said bobbin is caused to protrude from the top end of said housing, thereby providing a visual indication that said tube has retracted into said needle with said exit hole being at least partially blocked by an inside wall portion of said needle.

* * * * *

UNITED STATES PATENT AND TRADEMARK OFFICE
CERTIFICATE OF CORRECTION

PATENT NO. : 5,098,388
DATED : March 24, 1992
INVENTOR(S) : Richard Kulkaski, et. al.

It is certified that error appears in the above-indentified patent and that said Letters Patent is hereby corrected as shown below:

On the Title page, item [76], inventors: change "Kulkashi" to --Kulkaski--.

Signed and Sealed this

Ninth Day of November, 1993

Attest:

BRUCE LEHMAN

Attesting Officer

Commissioner of Patents and Trademarks